_United States Patent_ [19]

Hayes et al.

[11] 4,419,342

[45] Dec. 6, 1983

[54] DENTIFRICE PREPARATION

[75] Inventors: Harry Hayes, Warrington; Kenneth Harvey, Wilmslow, both of England

[73] Assignee: Colgate-Palmolive Company, New York, N.Y.

[21] Appl. No.: 458,244

[22] Filed: Jan. 17, 1983

Related U.S. Application Data

[63] Continuation-in-part of Ser. No. 356,674, Mar. 10, 1982, abandoned.

[51] Int. Cl.$^3$ ............................ A61K 7/16; A61K 7/22
[52] U.S. Cl. ........................................ 424/54; 424/49; 424/57
[58] Field of Search .................................... 424/49–58

[56] References Cited

U.S. PATENT DOCUMENTS

| | | | |
|---|---|---|---|
| 3,934,000 | 1/1976 | Barth | 424/49 |
| 4,036,949 | 7/1977 | Colodney | 424/49 |
| 4,069,310 | 1/1978 | Harrison | 424/49 |
| 4,137,303 | 1/1979 | Gaffar et al. | 424/52 |
| 4,143,128 | 3/1979 | Kim et al. | 424/54 |
| 4,144,324 | 3/1979 | Crutchfield et al. | 424/54 |
| 4,177,258 | 12/1979 | Gaffar et al. | 424/52 |
| 4,183,915 | 1/1980 | Gaffar et al. | 424/52 |
| 4,238,476 | 12/1980 | Harvey | 424/52 |
| 4,264,580 | 4/1981 | Barberio | 424/57 |
| 4,301,143 | 11/1981 | Barberio | 424/57 |

_Primary Examiner_—Shep K. Rose
_Attorney, Agent, or Firm_—Robert L. Stone; Herbert S. Sylvester; Murray M. Grill

[57] ABSTRACT

A rheologically smooth opaque dentifrice containing a siliceous polishing material, at least about 35% by weight of water, sodium alkyl sulfate surface active agent wherein the alkyl group contains 10–18 carbon atoms, with about 40–70% being $C_{12}$ and about 0.1–15% by weight of an alkylene diamine tetramethylene phosphonic acid water soluble salt.

5 Claims, No Drawings

DENTIFRICE PREPARATION

This application is a continuation-in-part of application Ser. No. 356,674 filed Mar. 10, 1982, now abandoned.

This invention relates to a dentifrice preparation. More particularly, it relates to a dentifrice preparation which has a rheologically smooth surface appearance.

Dentifrices containing polishing materials including certain siliceous polishing agents having a refractive index of about 1.44–1.47 have desirable cosmetic effects in the cleaning and polishing of tooth surfaces. The dentifrices are also compatible with many hygenic and prophylactic agents such as cariostatic compounds which provide fluoride. Further, they may be used to formulate visually clear (that is, translucent or transparent) dentifrice preparations. The dentifrice formulae may also be modified by including elevated amounts of water and/or opacifying agents in order to render the dentifrices opaque.

Dentifrice preparations containing such siliceous polishing agents, may appear to the beholder to be rheologically somewhat deformed in that lumps appear to be present when an elevated amount of water (say, at least about 35% by weight) is present. This is particularly so when the dentifrice is opaque so that only the surface is visible. Lumping becomes a particular problem when the preparation has been stored under cool temperature conditions. These lumps are quite soft and do not negatively affect extrusion of the dentifrice from its package. Further, they are not felt when the dentifrice is brushed on the teeth and dispersed in the oral cavity. Nevertheless, due to their appearance, the lumps may dissuade some potential customers from using what is in reality a hygenically desirable and beneficial dentifrice preparation.

The problem of soft lump formation particularly occurs when the opaque dentifrice contains at least about 35% by weight of water and sodium alkyl sulphate having a broad distribution of alkyl groups containing 10–18 carbon atoms. The reference to "water" refers to water which is free of association with a particular ingredient of the dentifrice such as water present to dissolve sorbitol.

It is an advantage of this invention that a dentifrice preparation is provided which is smooth without substantial rheological deformation. Further advantages will be apparent from consideration of the following disclosure.

In accordance with certain of its objects, this invention relates to an opaque dentifrice preparation comprising a liquid vehicle which contains at least about 35% by weight of water, up to about 10% by weight of a gelling agent, and about 10–50% by weight of a polishing material at least a major portion of which is a siliceous polishing material having an empirical $SiO_2$ content of at least 70%, a particle size in the range from 1 to 35 microns, substantially amorphous X-ray structure and a refractive index of about 1.40–1.47, about 0.1–5% by weight of a surface active agent containing sodium alkyl sulphate wherein the alkyl group contains 10–18 carbon atoms, with about 40–70% of the alkyl groups being $C_{12}$ and about 0.1–15% by weight of a water-soluble, orally acceptable salt of an alkylene diamine tetramethylene phosphonic acid, wherein the alkylene group contains 1–10 carbon atoms.

In British Pat. Nos. 1,599,690 and 1,599,689 (corresponding to U.S. Pat. Nos. 4,264,580 and 4,301,143) grain formation at low temperatures (e.g. about $-7°$ to $7°$ C.) in dentifrices containing calcium carbonate polishing agent and sodium alkyl sulphate with a broad distribution about $C_{10}$–$C_{18}$ alkyl groups is reduced by employing an alkali metal pyrophosphate or an anionic phosphate ester. Alkylene diamine tetramethyl phosphonic acid salt was not used. Indeed, it is known from British Pat. No. 1,344,185 that it is preferred not to use calcium carbonate in a dentifrice together with alkylene diamine tetraphosphonic acid salt.

In the present invention it was found that soft lumps which form, particularly upon aging at low temperature such as about $-7°$ to $7°$ C. could be reduced in a dentifrice containing a polishing material based on sodium aluminosilicate or silica containing combined alumina, an unassociated water level of at least about 35% by weight of the dentifrice and a surface active material including sodium alkyl sulphate having a broad alkyl distribution of about 10 to 18 carbon atoms by including $C_1$–10 alkylene diamine tetraphosphonic acid alkali metal salt in the dentifrice.

From the point of view of rheological appearance, soft lump formation is even more serious than graininess. A dentifrice is of poor appearance when deformed by lumps.

The proportion of the polishing agent of high silica content is in the range from 5% to 50% of the dentifrice, preferably from 10% to 30%, such as from 15% to 25%. One abrasive is an amorphous alkali metal or alkaline earth metal aluminosilicate (that is, silica containing combined alumina) having a refractive index of from 1.40 to 1.47, such as 1.44 to 1.47, and containing at least 70% silica, up to 10%, typically about 0.1–10% alumina, up to 20% of moisture and up to 10% of sodium oxide. Typically, this material has a particle size in the range from 1 to 35 microns, preferably from 2 to 20 microns, e.g. 2 to 4 microns. The preferred moisture content is from 10% to 20% measured by ignition at 1000° C. and the typical content of sodium oxide is from 0.5% to 10%. Generally, the polishing agent has a loose bulk density of up to 0.2 g/cc, such as from 0.07 to 0.12 g/cc. Another suitable type of polishing agent is porous amorphous silicic anhydride having an average particle size preferably below 20 microns and above 1 micron, a surface area of at least 200 $m^2/g$, preferably at least 300 $m^2/g$, and bulk density of at least 0.15 $g/cm^3$, preferably at least 0.30 $g/cm^3$, such as a dehydrated silica hydrogel (i.e. a xerogel), preferably of the well known regular density or intermediate density type. Examples of such amorphous silicic anhydride polishing agents are "Syloid 63", "Syloid 72", and "Syloid 74" (SYLOID is a trade mark) which are described in "The Davison Family of Syloid Silicas" published by their manufacturers, Grace, Davison Chemical Company. "Santocel 100" of Monsanto (SANTOCEL is a trade mark), is also a suitable dental abrasive. "Syloid 72" has an average Particle size of about 4 microns, a surface area of about 340 $m^2/g$ and a bulk density of about 1.77 $g/cm^3$. For "Syloid 63" the corresponding figures are about 9 microns, about 675 $m^2/g$ and about 0.4 $g/cm^3$. A grade of "Santocel 100" has a surface area of about 239 $m^2/g$ and a bulk density of about 0.24 $g/cm^3$. These amorphous silicic anyhdrides may be used singly or in mixtures.

When the siliceous polishing agent amounts to at least about 10% by weight of the dentifrice, it may be the only polishing agent present. If desired the siliceous polishing agent may be present in major amount (at least half of the polishing material) with regard to a further polishing agent or polishing agent mixture. The further polishing agent may be dentally acceptable polishing agents such as calcined alumina, alpha-alumina trihydrate, dicalcium phosphate dihydrate, anhydrous dicalcium phosphate, insoluble sodium metaphosphate, calcium carbonate and the like, including mixture thereof. Calcined alumina is preferred. The further polishing agent, (including mixtures thereof) is typically present in amount of about 5–20% not exceeding the amount of siliceous polishing agent. The further polishing material deepens the opaqueness. of the dentifrice.

The surface active agent includes sodium alkyl sulphate having a broad distribution of alkyl groups containing 10–18 carbon atoms.

Sodium lauryl sulphate has long been used in dentifrice compositions but it has generally been used as a "narrow cut" material in which at least 90%, even 99% of the alkyl groups are $C_{12}$. Dental creams containing siliceous polishing agent and "narrow cut" sodium lauryl sulphate often do not become lumpy even upon aging at low temperatures. Commercially available grades of "narrow cut" sodium lauryl sulphate include Empicol 0045 available from Marchon Division of Albright & Wilson, Texapon K 1296 available from Henkel and Cie. and Alfol 12 available from Conoco.

When sodium alkyl sulphate of broader alkyl distribution is employed, the problem of lumping upon aging at low temperature can be recognized. A particular sodium lauryl sulphate employed for the present invention contains about 3% $C_{10}$; 56% $C_{12}$; 21% $C_{14}$; 9% $C_{16}$ and 11% $C_{18}$ alkyl groups and is commercially available in the form of needles as Empicol "LZV" from Marchon Division of Albright and Wilson, Whitehaven, England. Further broad cut grades of sodium alkyl sulphate which may be employed are Tensopol SP ACL7 from Tensia S. A., Leige, Belgium and Texapon ZHC from Henkel and Cie., Dusseldorf, West Germany. Such grades of sodium alkyl sulphate include in their alkyl distribution about 40 to 70% $C_{12}$. More particularly, they typically have an alkyl distribution of about 1 to 8% $C_{10}$: 40 to 70% $C_{12}$, 13 to 30% $C_{14}$, 5 to 16% $C_{16}$, and 0–23% $C_{18}$. The alkyl groups are substantially straight chain (normal).

The sodium alkyl sulphate may be prepared by means known in the art to give a product with broad alkyl distribution. "Narrow cut" sodium lauryl sulfate would be prepared from the broader cut material by fractional distillation and recrystallisation.

In addition to sodium alkyl sulphate of broad alkyl distribution, the dentifrice optionally may include an additional surface active agent. Such agents may include anionic materials, for instance, water-soluble salts of higher fatty acid monoglyceride monosulphate (e.g. sodium coconut fatty acid monoglyceride monosulphate), alkyl aryl sulphonate (e.g. sodium dodecyl benzene sulphonate), higher fatty acid esters of 1,2-dihydroxy propane sulphate (e.g. sodium coconut fatty acid ester of 1,2-dihydroxypropane sulphonate) etc.

A nonionic or ampholytic surface active agent may also be present, such agents including nonionic agents such as sorbitan monostearate with approximately 20 moles of ethylene oxide, condensates of ethylene oxide with propylene oxide (available under the trademark "Pluronics") and amphoteric agents such as quaternized imidazole derivatives which are available under the trademark "Miranol" such as Miranol C2M. It is preferred that the total amount of surface active agent does not exceed about 5% by weight of the oral composition. The total surface active material content of the dentifrice is typically about 0.1 to 5% by weight. Preferably about 1 to 2% by weight of sodium alkyl sulphate of broad alkyl distribution is present.

The additive which reduces the lump formation, particularly aging at low temperature, such as about $-7°$ to $7°$ C., is a water soluble, orally acceptable salt of an alkylene group contains 1–10 carbon atoms. Such salts have the formula:

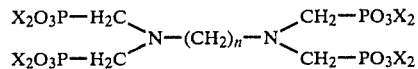

wherein n is a number from 1 to 10 and X is hydrogen or orally acceptable cation such as alkali metal (e.g., sodium and potassium), ammonium, $C_1$–$C_{18}$ mono-, di and tri-substituted ammonium (e.g., mono-, di-, and triethanolammonium salts, with the proviso that up to 7, preferably 3–5 of the "X" groups may be hydrogen.

The polyamine polyphosphonic compounds which are most preferred are water soluble orally acceptable salts (most preferably tri-, tetra-, or penta-sodium salts of ethylenediamine tetra (methylenephosphonic acid), (hereinafter EDITEMPA.)

Other polyamine polyphosphonic compounds include orally acceptable water-soluble salts of tetramethylenediamine tetra (methylenephosphonic acid), pentamethylene diamine tetra (methylenephosphonic acid), hexamethylene diamine tetra (methylenephosphonic acid) and octamethylene diamine tetra (methylenephosphonic acid).

The polyamine polyphosphonates salts thereof can be prepared in any convenient manner, for example according to the teachings of U.S. Pat. No. 3,288,846 or Moedritzer and Irani, Journal of Organic Chemistry, May 1966, pages 1603–1607.

The concentration of polyamine polyphosphonates in dentifrices can range widely, typically from about 0.1 to 15% by weight. Generally, concentrations from about 0.5 to about 5% by weight are utilized.

The opaque dentifrice is typically a toothpaste containing a gel or liquid vehicle, preferably as a mass of a consistency which can be extruded from a collapsible tube such as an aluminum tube or a lead tube. The vehicle contains liquid and solids. The liquid portion comprises water and generally a humectant such as glycerine, aqueous sorbitol or polyethylene glycol. The total liquid content is at least about 35%, at least about 35% by weight of the dentifrice being water (not associated with humectant), typically about 35–50%, and humectant (including water associated with humectant), if any, typically about 25–50%, by weight of the dentifrice. The elevated water content serves to render the dentifrice opaque, particularly when a polishing agent further to the siliceous polishing agent is present.

In the liquid portion of the vehicle, sorbitol is suitably employed as a 70% aqueous solution. Glycerine alone or admixed with the sorbitol is also a very suitable humectant.

The solid portion of the vehicle is a gelling agent such as a natural or synthetic gum or gum-like material, such as Irish Moss, gum tragacanth, alkali metal carboxymethyl cellulose, polyvinyl pyrrolidone, starch, water-soluble hydrophilic collodial carboxyvinyl polymer such as those sold as "Carbopol 934" and "Carbopol 940" (CARBOPOL is a trade mark), and synthetic inorganic silicated clays such as those sold as "Laponite CP" and "Laponite SP" (LAPONITE is a trade mark). These grades of "Laponite" have the formula $(Si_8Mg_{5.1}Li_{0.6}O_{24})^{0.6-}Na^+_{0.6}$. The solid portion of the vehicle is typically present in an amount up to 10% of the dentifrice, preferably from 0.5% to 5%. When employed grades of "Laponite" are preferably used in amounts of from 1% to 5%.

Any suitable flavouring or sweetening materials may be employed in formulating a flavour for the dentifrices. Examples of suitable flavouring constituents include flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, dipeptides as described in U.S. Pat. No. 3,939,261, oxathiazin salts as described in U.S. Pat. No. 3,932,606, perillartine and saccharine. Suitably, flavour and sweetening agents may together constitute from 0.01% to 5% or more of the dentifrice. Chloroform may also be used.

Various other adjuvant materials may be incorporated in dentifrices of this invention. Examples are pigments such as titanium dioxide and zinc oxide, preservatives, silicones chlorophyll compounds, and ammoniated materials such as urea, diammonium phosphate and mixtures thereof. The adjuvants are incorporated in the dentifrices in amounts which do not substantially adversely affect the properties and characteristics desired.

Antibacterial agents may also be employed in the dentifrice of the invention, e.g. in an amount in the range from 0.01% to 5% by weight. Typical antibacterial agents include:

$N^1$-(4-chlorobenzyl)-$N^5$-(2,4-dichlorobenzyl) biguanide;
p-chlorophenyl biguanide;
4-chlorobenzlhydryl biguanide;
4-chlorobenzylhydrylguanylurea;
N-3-lauroxypropyl-$N^5$-p-chlorobenzylbiguanide;
1,6-di-p-chlorophenylbiguanidohexane;
1,6-bis(2-ethylhexylbiguanido) hexane;
1-(lauryldimethylammonium)-8-(p-chlorobenzyldimethyl ammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine; and their non-toxic acid addition salts.

Synthetic finely divided silicas such as those sold as the "Cab-O-Sil M-5", "Syloid 244", "Syloid 266", "Aerosil D200" and mixtures thereof, may also be employed, e.g. in amount of from 0.5% to 20%, to promote thickening or gelling (CAB-O-CIL, SYLOID and AEROSIL are trade marks).

A toothpaste dentifrice may be prepared by forming a gel with humectant, gum or thickener, sweetener and water and adding thereto polishing agent, surface active agent, EDITEMPA salt or the like and flavour. Alternatively the EDITEMPA salt or the like may be added during gel stage manufacture.

The dentifrice should have a pH practicable for use e.g. about 4-10.5, preferably about 7.5-10.5. The pH may be adjusted with appropriate materials known in the art, such as sodium hydroxide.

The following examples illustrate the invention. All parts and proportions are by weight unless otherwise indicated.

EXAMPLE 1

The following opaque dentifrices are prepared and placed in aluminum tubes having an inner lacquered lining;

| INGREDIENTS | PARTS A | PARTS B |
|---|---|---|
| Glycerine | 25.00 | 25.00 |
| Sodium carboxymethyl cellulose | 1.10 | 1.10 |
| Titanium Dioxide | 0.40 | 0.40 |
| Saccharin acid | 0.12 | 0.12 |
| Silica combined with alumina (Alusil N - RI 1.45 available from Joseph Crosfield and Sons, Ltd. Warrington, England) | 20.00 | 20.00 |
| Calcined alumina (MAF-Microgrit available from British Aluminum Company) | 10.00 | 10.00 |
| EDITEMPA Na$_{4-6}$ salt | — | 2.00 |
| Sodium alkyl sulphate LZV available from Marchon Division of Albright & Wilson | 1.76 | 1.76 |
| Flavour | 1.20 | 1.20 |
| Water | 41.42 | 39.42 |
| pH (20% slurry) | 10.2 | 10.2 |

Upon extrusion of a ribbon of each dentifrice from the tube, Dentifrice A has a lumpy surface appearance whilst Dentifrice B containing salt of EDITEMPA has a rheologically smooth surface appearance.

EXAMPLE 2

Similar results to those of Example 1 are obtained when 0.82 parts of sodium monofluorophosphate are included in each of dentifrices A and B with the water contents being reduced to 40.60 parts and 38.60 parts respectively (pH of 20% slurries—A 9.8; B 8.56).

It will be apparent to those skilled in the art that modifications of the above examples may be made thereto.

We claim:

1. An opaque dentifrice comprising a liquid vehicle which contains at least about 35% by weight of water, up to about 10% by weight of gelling agent, about 10-50% by weight of a polishing material at least a major portion of which is a siliceous polishing material having an empirical $SiO_2$ content of at least 70%, a particle size in the range from 1 to 35 microns, substantially amorphous X-ray structure and a refractive index of about 1.40-1.47 and as an additional polishing agent an amount of about 5-20% by weight of the dentifrice of a dentally acceptable polishing agent selected from the group consisting of calcined alumina, alpha-alumina trihydrate, dicalcium phosphate dihydrate, anhydrous dicalcium phosphate, insoluble sodium metaphosphate, calcium carbonate and mixtures thereof, said amount of said additional polishing agent not exceeding the amount of said siliceous polishing agent, about 0.1-5% by weight of a surface active agent containing sodium alkyl sulphate wherein the alkyl group contains 10-18 carbon atoms, with about 40-70% of the alkyl groups being $C_{12}$ and about 0.1-15% by weight of a water soluble, orally acceptable salt of an alkylene diamine tetramethylene phosphonic acid, wherein the alkylene group contains 1-10 carbon atoms, said dentifrice being smooth and without substantial soft lump rheological deformation.

2. The dentifrice preparation claimed in claim 1 wherein calcined alumina is present as said additional polishing material.

3. The dentifrice preparation claimed in claims 1 wherein said sodium alkyl sulphate has the following alkyl group distribution: about 1–8% $C_{10}$; 40–70% $C_{12}$; 13–30% $C_{14}$; 5–16% $C_{16}$; and 0–23% $C_{18}$, all percents being by weight.

4. The dentifrice preparation claimed in claim 1 wherein said salt of alkylene diamine tetramethylene phosphonic acid is the tetra-, penta- or hexa-sodium salt of ethylene diamine tetra (methylenephosphonic acid).

5. The dentifrice preparation claimed in claims 1, 2, 3 or 4 wherein said siliceous polishing material has a refractive index of about 1.44 to 1.47.

* * * * *